United States Patent [19]

Ito

[11] Patent Number: 5,411,020
[45] Date of Patent: May 2, 1995

[54] STRUCTURE OF THE DISTAL END PORTION OF AN ENDOSCOPE

[75] Inventor: Keiji Ito, Tokyo, Japan

[73] Assignee: Asahi Kogaku Kogyo Kabushiki Kaisha, Tokyo, Japan

[21] Appl. No.: 113,353

[22] Filed: Aug. 30, 1993

Related U.S. Application Data

[63] Continuation of Ser. No. 797,978, Nov. 26, 1991, abandoned.

[30] Foreign Application Priority Data

Nov. 27, 1990 [JP] Japan .................. 2-126126 U

[51] Int. Cl.⁶ ............................................. A61B 1/04
[52] U.S. Cl. ........................................................ 128/4
[58] Field of Search ...................................... 128/4–10; 604/283

[56] References Cited

U.S. PATENT DOCUMENTS

| 4,757,819 | 7/1988 | Yokoi et al. ............... 128/4 X |
| 5,005,558 | 4/1991 | Aomori ..................... 128/4 |
| 5,022,383 | 6/1991 | Sakiyama et al. ......... 128/6 |

Primary Examiner—Richard J. Apley
Assistant Examiner—John P. Leubecker
Attorney, Agent, or Firm—Sughrue, Mion, Zinn, Macpeak & Seas

[57] ABSTRACT

The distal end body of an endoscope containing an objective optical system or other components is coupled with the distal end of a bendable portion by a coupling tube. The rear end of the coupling tube is fitted on the inside of the foremost end part of the bendable portion and is fixed to the foremost end part of the bendable portion at fixing locations. Portions of the coupling tube proximate the fixing locations have a greater thickness while remaining locations have a lesser thickness, so as to provide adequate mechanical strength while maximizing the interior cross sectional area of the coupling tube.

5 Claims, 4 Drawing Sheets

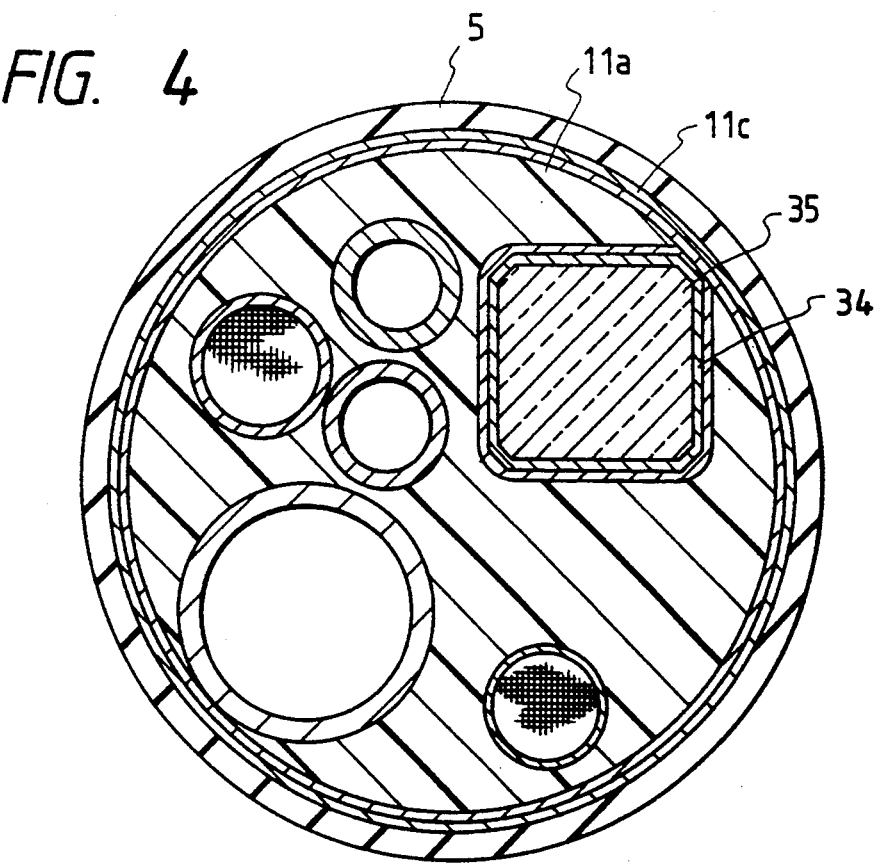
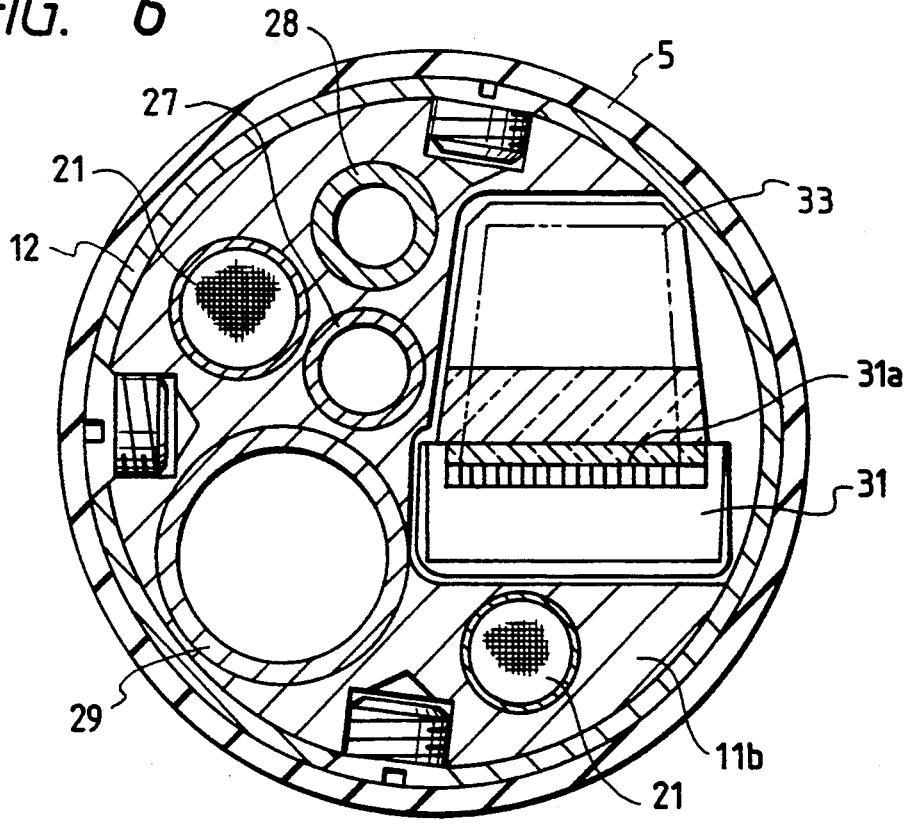

STRUCTURE OF THE DISTAL END PORTION OF AN ENDOSCOPE

This is a Continuation of Application Ser. No. 07/797,978 filed Nov. 26, 1991, now abandoned.

BACKGROUND OF THE INVENTION

This application is based on and claims priority from Japanese Application No. HEI 2-126126 filed Nov. 27, 1990, the disclosure of which is incorporated by reference herein.

The present invention relates to a structure of the distal end portion of an endoscope, and more particularly to the structure of a coupling tube located between a distal end body and a bendable portion of an endoscope.

In some electronic endoscopes, a coupling tube is used for coupling a bendable portion and a distal end body containing an objective optical system, in order to accommodate parts such as the solid-state image pickup element and the like.

In this type of the endoscope, the coupling tube is fitted to the inside, or outside, of the nodal ring of the foremost end of the bendable portion, and fixed by screws or another suitable fixing means.

When the coupling tube is fitted to the outside of the nodal ring, the distal end portion at that location is necessarily increased in diameter. The result is to hinder the smooth insertion of the endoscope into a body cavity and to consequently cause increased discomfort or pain to patients when the endoscope is inserted.

When the coupling tube is fitted to the inside of the nodal ring, the inner diameter of the coupling portion is decreased so as to reduce the space available therein for accommodating contained members, such as tubes and a light guide fiber bundle for illumination. This limits the performance of the endoscope, and attempting to avoid this performance impairment by increasing the diameter of the coupling portion leads to poor insertion of the endoscope and greater discomfort to the patient as discussed above.

SUMMARY OF THE INVENTION

The present invention has been made in view of the above circumstances, and it is an object of the invention to provide a structure of the distal end portion of an electronic endoscope with an inner diameter large enough to accommodate the necessary contained members without increasing the outer diameter of the coupling part of the bendable portion and the coupling tube for coupling the bendable portion with the distal end body.

To achieve the above object, the distal end body containing, e.g., an objective optical system, is coupled with the distal end of a bendable portion by means of a coupling tube. The rear end portion of the coupling tube is fitted on the inside of the foremost end part of the bendable portion, the coupling tube is fixed to the foremost end part of the bendable portion by a fixing means, and the coupling portion of the coupling tube has a decreased diameter at least at portions proximate the fixing means.

With such a structure, a space large enough to accommodate the respective members to be contained within the distal end portion is ensured. The inner diameter of the coupling tube, with the exception of areas proximate the fixing means, approaches the inner surfaces of the foremost end part of the bendable portion and allows the contained members to be passed therethrough.

BRIEF DESCRIPTION OF THE DRAWINGS

The invention will be more clearly understood from the following detailed description of the preferred embodiment of the invention with reference to the accompanying drawings, wherein:

FIG. 4 is a cross sectional view taken on line IV—IV in FIG. 2;

FIG. 6 is a cross sectional view taken on line VI—VI in FIG. 2; and

DETAILED DESCRIPTION OF THE PREFERRED EMBODIMENT

The preferred embodiment of the structure of the distal end portion of an endoscope will now be described in detail with reference to the accompanying drawings.

Figure 1:
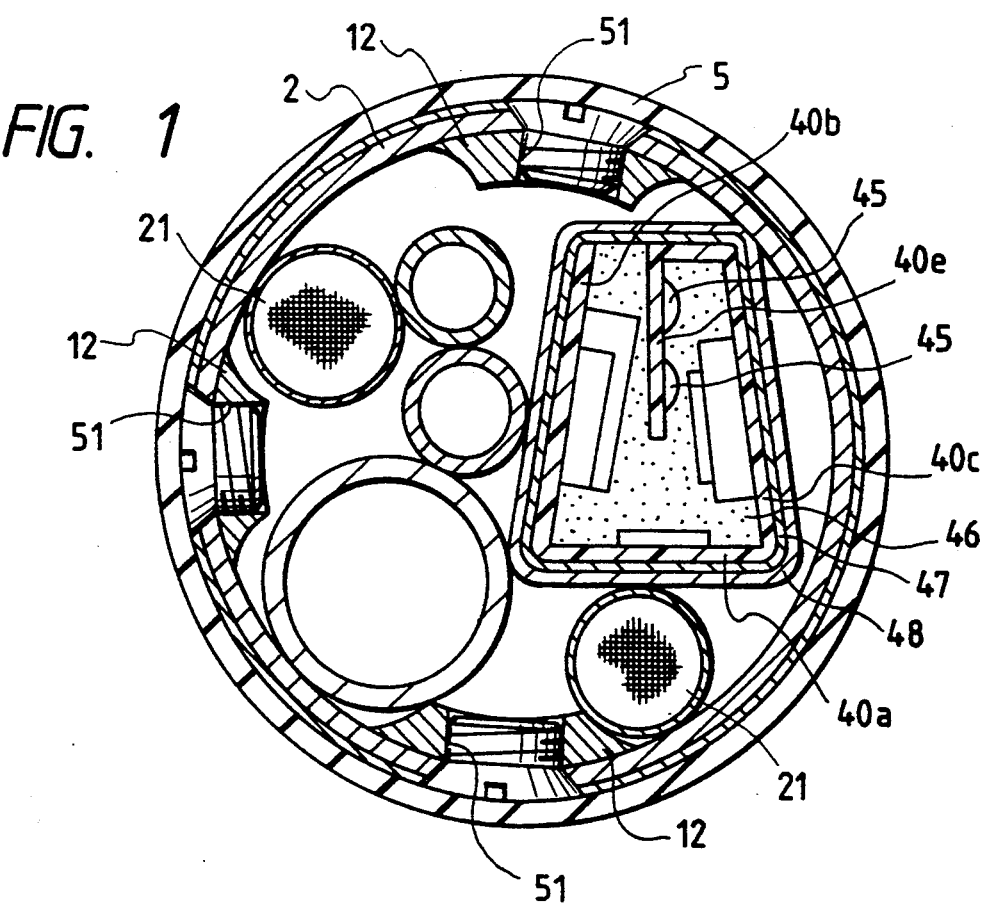
FIG. 1 is a cross sectional view taken on line I—I in FIG. 2.
Figure 2:
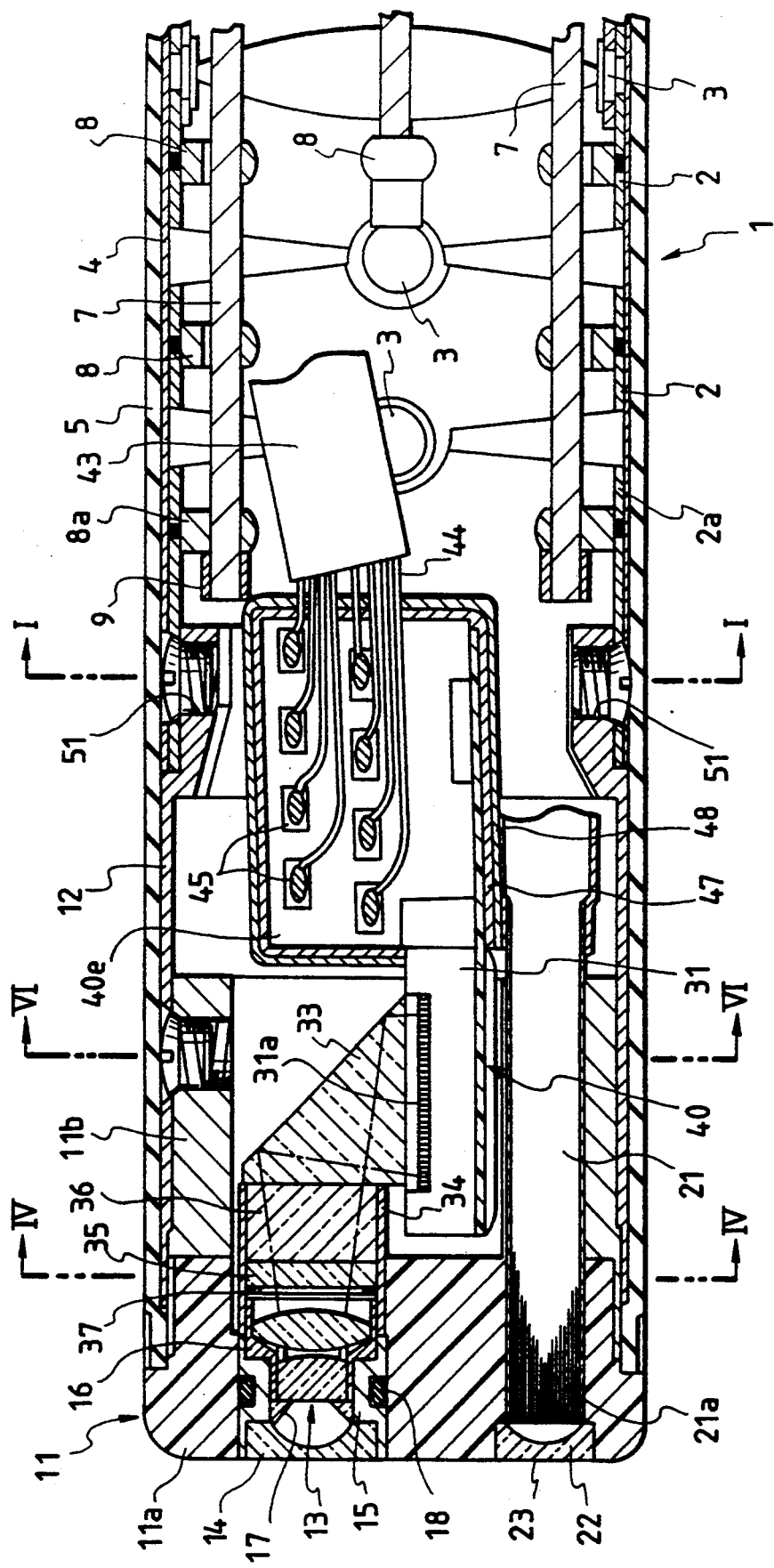
FIG. 2 is a longitudinal sectional view showing the structure of the distal end portion of an endoscope according to an embodiment of the present invention.

FIG. 2 is a longitudinal sectional view showing the structure of the distal end portion of an endoscope according to an embodiment of the present invention. In FIG. 1, bendable portion 1 of the distal end of a slender, flexible pipe, serves as an insertion portion of the endoscope. In bendable portion 1, a plurality of nodal rings 2 are rotatably coupled with each other by means of rivets 3. Nodal rings 2 are covered with mesh tube 4 made of fine metal wires, or the like, and sheathing tube 5 made of rubber, or the like.

Bendable, operating wires 7, which can be remotely manipulated, are retractably placed within wire guides 8 which protrude inwardly from nodal rings 2 respectively. The tip of bendable operating wires 7 are fixed to wire guide 8 which is provided in the nodal ring 2a closest to the distal end of the insertion portion, by silver brazing, for example. Stopper pipe 9, for preventing operating wire 7 from slipping off of wire guide 8, is fixed to the end of wire guide 8 by silver brazing.

Distal end body 11 is coupled with the tip of bendable portion 1 by means coupling tube 12. Distal end body 11 is formed with metal body part 11b and head part 11a, made of electrically insulating plastic, which is coupled with distal side of the metal body 11b. Distal end body 11 is circular in cross section when seen from the end (the left side in FIG. 2). Objective optical system 13 is contained within head part 11a.

Objective optical system 13 consists of a plurality of lenses, and is contained in, and axially coincident with, distal end body 11. Light from an observed object is made incident to the incident side surface of the objective optical system (the left side in FIG. 2). View window 14 is defined by the foremost lens of objective optical system 13. Lens barrel 15 and 16 are provided for holding respective lenses of objective optical system 13. Outer lens barrel 15 is bonded to head part 11a of distal end body 11. Aperture diaphragm 17 is provided immediately behind view window 14, and O-ring 18 is provided for sealing purposes between head port 11a and lens barrel 15.

Light emitting end 21a of light guide fiber bundle 21 is secured to head part 11a of distal end body 11, having its axis parallel to objective optical system 13. Concave lens 22, for dispersing illumination emitted from fiber bundle 21 is disposed on the distal end face of light emitting end 21a. Thus, concave lens 22 defines an illumination window 23. Light transmitted through fiber bundle 21 illuminates objects located ahead of distal end body 11.

Figure 3:
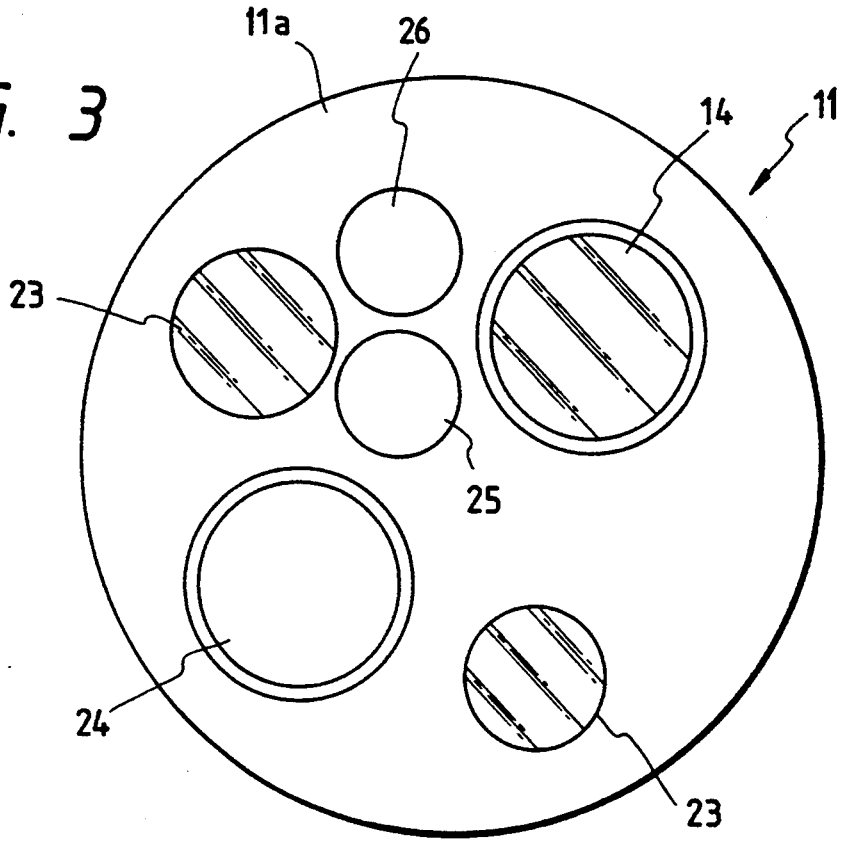
FIG. 3 is a front view showing the endoscope of FIG. 2.

FIG. 3 is a front view of head part 11a of distal end body 11. As shown, two illumination windows 23 are provided, and a respective fiber bundle 21 is disposed on the inner side of each illumination window 23. Port 24 allows surgical instruments, e.g., forceps, to be inserted through the endoscope and for suction. Air-feed nozzle 25 and water-feed nozzle 26, are also provided within head part 11a to clean the surface of the view window 23.

Returning to FIG. 2, solid-state image pick-up element 31 is disposed within body part 11b. Solid-state image pick-up element 31 may be a CCD (charge coupled diode), or the like. Light receiving surface 31a of solid-state image pick-up element 31 is rectangular or square, and disposed in a plane that is parallel with the center axis of objective optical system 13, so that the center axis of the objective optical system 13 is perpendicular to the center axis of the light-receiving surface 31a. Prism 33 is disposed between objective optical system 13 and the pick-up element 31, to direct light passing through objective optical system 13 onto the light receiving surface 31a.

Optical coupling tube 34 coupled with the latter half of the lens barrel 16 has a series of color correction filters 35 contained therein, and low-pass filter 36 is disposed between prism 33 and objective optical system 13. With such a structure, an image of an object (not shown) located on the left side of view window 14 in FIG. 2 is formed on light receiving surface 31a of the solid-state image pick-up element 31, through objective optical system 13 and prism 33.

As shown in FIG. 4, optical coupling tube 34 and the optical elements disposed therewithin are shaped to substantially define a square in cross section, with the four corners thereof which are in order to transmit the light beam, cut off. In this embodiment, objective optical system 13 is designed such that principal rays traveling from the observed object through the objective optical system 13 to solid-state image pick-up element 31 gradually diverges as indicated by one-dot-chain lines in FIG. 2.

Solid-state image pick-up element 31, unlike conventional light guide fiber bundles, is capable of receiving light with low loss even if light is relatively obliquely incident thereon. It is for this reason that objective optical system 13 can be of a type in which a principal ray diverges. With use of objective optical system 13, the outer configuration of the rays of light passing through prism 33 also gradually diverges toward light receiving surface 31a, as indicated by a two-dot-chain line in FIG. 6, when viewed from objective optical system 13.

Prism 33 is shaped like a trapezoid of which nonparallel sides gradually diverge toward the light receiving surface 31a, i.e., it is substantially parallel to the outer configuration of the light passing therethrough as shown in FIG. 6. The shape of prism 33 minimizes the area occupied thereby in the cross sectional area of distal end body 11, thereby allowing the distal end body 11 itself to be small in cross section.

Figure 5:
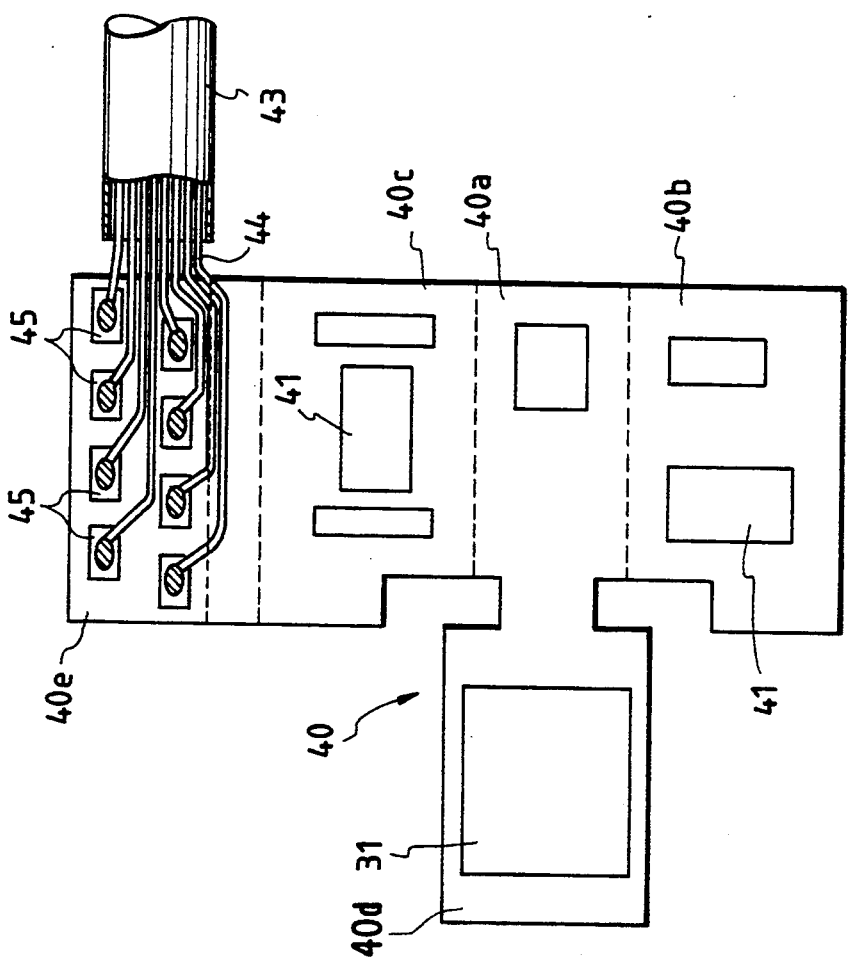
FIG. 5 is a development of a circuit board used in the embodiment of FIG. 2.

In FIG. 6, air-feed pipe 27, water-feed pipe 28, and surgical instrument insertion pipe 29 (for forceps, or the like) can be seen. Circuit board 40, to which solid-state image pick-up element 31 is mounted, consists of a flexible, electrically insulating plastic plate, as shown in FIG. 5.

Circuit board 40 is divided into five planar surfaces 40a–40e. (see FIG. 5). These five surfaces can be folded along broken lines, which extend in the axial direction of distal end body 11, so as to assume a traperzoidal cross-sectional shape as indicated in FIG. 1. Electronic circuits coupled with solid-state image pick-up element 31 are formed on planes 40b and 40c, which are on both sides of plane 40a having solid-state image pick-up element 31 mounted thereon. Various types of electronic parts such as part 41, for example, are mounted on planes 40b and 40c. Terminals 45 which are electrically connected to the electronic circuits are formed on the uppermost plane 40e of circuit board 40 as viewed in the drawing. Lead wire 44 of cable 43, which is inserted into bendable portion 1 from the flexible tube portion of the endoscope, is soldered to terminal 45.

Circuit board 40, shaped like a trapezoid, as viewed from objective optical system 13, is similar in shape to the outer configuration of the prism 33, as shown in FIG. 6. Circuit board 40 is located on the rear side of the prism 33, at a position proximate thereto. Accordingly, the outer edge of prism 33 closely overlaps with bent circuit board 40 when seen from the objective optical system 13.

Figure 7:
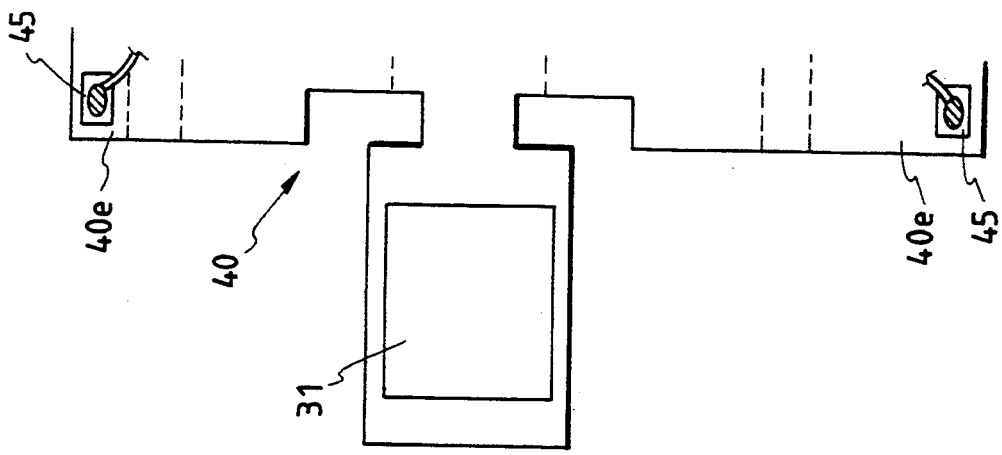
FIG. 7 is a development of another circuit board used in the embodiment of FIG. 2.

Plane 40e, having terminals 45, is bent downward at the center of the upper shorter side of the trapezoid defined by circuit board 40. The space within the trapezoid of the circuit board is filled with electrically insulating plastic, or the like. Accordingly, terminals 45 extend neither axially nor laterally from circuit board 40, leading to reduction in the length and width occupied by circuit board 40. In case two cables 43 are used, it is advisable to construct circuit board 40 having two planar surfaces 40e with terminals 45 and which can be folded along dotted lines so as to extend inward on both ends thereof as shown in FIG. 7, to which lead wires are soldered respectively.

An outer peripheral surface of circuit board 40, after being folded and shaped like a trapezoid, is covered by electrical conducting body 47 along the surface of circuit board 40 so as to form an electrical shielding layer.

Electrical conducting body 47 is also shaped like a trapezoid as viewed from objective optical system 13. Further, an outer surface of electrical conducting body 47 is covered by electrical insulating member 48 in such a manner that an electrical current leakage is prevented from occurring.

Returning to FIG. 2, coupling tube 12, surrounding circuit board 40, is tubular in shape, with the exception of the rear part thereof (right side in FIG. 2). The distal part of coupling tube 12 is fitted around body part 11b. A rear portion of coupling tube 12 is fitted into and fixed to foremost nodal ring 2a by means of screws. As illustrated in FIG. 2, the rear portion of coupling tube 12 has an outer diameter which is the same as or smaller than the inner diameter of the distal portion of coupling tube 12.

To form holes 51 for receiving screws, portions of coupling tube 12, proximate holes 51, have a smaller inner diameter than the remaining portions. That is, the wall thickness of portions of the coupling tube 12 proximate holes 51 is greater than in the remaining portions of the tube 12. More specifically, the rear end portion of coupling tube 12 is thicker, and portions other than in the vicinity of the three screw holes 51 are machined out so as to be cut off to define apertures. As a result, within the rear end portion of coupling tube 12, a space large enough to accommodate the members to be contained therein is defined, while holes 51 are reinforced to provide adequate strength. In portions of coupling tube 12 other than in the area of the holes 51, the diameter approaches the circumferential inner surfaces of nodal rings 2 so as to allow the respective contained members, such as a fat surgical channel and the light guide fiber bundle 21, to be easily passed therethrough it can be seen that the interval between each thick portion of coupling tube 12 is not more than 180 degrees (see FIG. 1).

In the above-mentioned embodiment of the invention, the rear end portion of coupling tube 12, other than three portions in the proximity of screw holes 51 formed therein, are machined so as to be cut off. However, it is also possible to employ a coupling tube having a rear end portion in which only portions interfering with accommodated respective members to be contained in coupling tube are machined out so as to be cut off.

Instead of machining the inner wall down from an initial greater thickness, coupling tube 12 may initially have a uniform inner diameter and may be built up in the area of the holes 51.

Coupling tube 12 may be coupled with foremost nodal ring 2 by means of any suitable coupling means other than screws, such as silver brazing and spot welding.

While in the embodiment described above the rear part of coupling tube 12 is fitted into and fixed to foremost nodal ring 2 at three locations using three screws, it may be connected at one location or more than three locations by a corresponding number of screws, or the like. Sheathing tube 5 covers the rear part of distal end body 11.

As seen from the foregoing description, according to the present invention, coupling tube 12 is fitted to the inside of the foremost end part of the bendable portion 1. Accordingly, the outer diameter of the coupling portion will not exceed the outer diameter of the bendable portion. The structure provides for easy insertion of the endoscope so as to be more comfortable for patients.

Further, since the coupling portion of coupling tube 12, except the fixing portions, is machined out, a space large enough to accommodate the necessary number of contained members passing therethrough is defined, thus realizing a satisfactory performance of the endoscope. It should be noted that the present invention can be applied to a fiber endoscope instead of an electronic endoscope as described.

While there has been described what is at the present considered to be the preferred embodiment of the invention, it will be understood by those skilled in the art that the foregoing and other changes in form and details can be made therein without departing from the spirit and scope of the invention.

What is claimed is:

1. An endoscope, comprising a bendable portion with a forward end, a distal end body having components therein, and a coupling tube having a first end coupled to said distal end body and a second end coupled to said bendable portion, said second end of said coupling tube being fitted inside said forward end of said bendable portion and fixed to said bendable portion at at least two fixing locations, an outer wall of said second end of said coupling tube being of a first thickness in regions proximate said fixing locations and having other regions which are disposed between each pair of said fixing locations, a sheathing tube covering said coupling tube;

wherein the inner diameter of said first end is at least as big as the outer diameter of said second end and said other regions have an aperture formed therein which extends through said outer wall, said aperture extends over a substantial portion of an angular interval defined between adjacent fixing locations and wherein each said angular interval is not more than 180 degrees.

2. An endoscope as claimed in claim 1, wherein said components include an optical system.

3. An endoscope as claimed in claim 1, wherein there are a plurality of said fixing locations.

4. An endoscope as claimed in claim 3, wherein said coupling tube is fixed to said bendable portion via fixing means comprising one of screws, silver brazing, and spot welding.

5. An endoscope as claimed in claim 1 wherein there are at least three of said fixing locations.

* * * * *